US012779153B2

(12) United States Patent
Latiman Da Silva Brito et al.

(10) Patent No.: US 12,779,153 B2
(45) Date of Patent: Nov. 3, 2026

(54) SYSTEM FOR INDICATING AN AT-RISK SITUATION FOR A LUNG VENTILATOR

(71) Applicant: Magnamed Tecnologia Medica S/A, São Paulo (BR)

(72) Inventors: Alecsandre Latiman Da Silva Brito, São Paulo (BR); Jonas Sona Pires, São José dos Campos (BR); Wataru Ueda, São Paulo (BR); Toru Miyagi Kinjo, São Paulo (BR); Tatsuo Suzuki, São Paulo (BR); Sandra Santana Souza, São Paulo (BR)

( * ) Notice: Subject to any disclaimer, the term of this patent is extended or adjusted under 35 U.S.C. 154(b) by 263 days.

(21) Appl. No.: 18/547,188

(22) PCT Filed: Feb. 23, 2022

(86) PCT No.: PCT/BR2022/050058
§ 371 (c)(1),
(2) Date: Aug. 21, 2023

(87) PCT Pub. No.: WO2022/178610
PCT Pub. Date: Sep. 1, 2022

(65) Prior Publication Data

US 2024/0148992 A1 May 9, 2024

(30) Foreign Application Priority Data

Feb. 23, 2021 (BR) ...................... 10 2021 003412 2

(51) Int. Cl.

| | |
|---|---|
| ***A61B 5/08*** | (2006.01) |
| ***A61M 16/00*** | (2006.01) |
| ***G06T 11/40*** | (2006.01) |
| ***G16H 40/63*** | (2018.01) |

(52) U.S. Cl.
CPC ............ *A61M 16/00* (2013.01); *G06T 11/40* (2013.01); *G16H 40/63* (2018.01); *G06T 2210/41* (2013.01)

(58) Field of Classification Search
CPC .......... A61M 16/00; A61M 2210/1039; A61M 2205/505; A61M 2205/583; A61M 2230/46; G06T 11/40; G06T 2210/41; G16H 40/63; A61B 5/742
See application file for complete search history.

(56) References Cited

U.S. PATENT DOCUMENTS

| | | | |
|---|---|---|---|
| 9,675,300 | B2 | 6/2017 | Orr et al. |
| 11,423,535 | B2 | 8/2022 | Wang et al. |
| 2009/0024008 | A1 | 1/2009 | Brunner et al. |

(Continued)

OTHER PUBLICATIONS

International Search Report dated Jun. 15, 2022 in International Application No. PCT/BR2022/050058.

(Continued)

*Primary Examiner* — Xiao M Wu
*Assistant Examiner* — George Renze
(74) *Attorney, Agent, or Firm* — B. Aaron Schulman, Esq.; Stites & Harbison, PLLC

(57) ABSTRACT

The present invention relates to a system for indicating an at-risk situation for a lung ventilator, comprising a screen (1) that displays at least one fixed-size drawing element (2) representing the lungs being ventilated, in which the shade of the drawing element switches according to predetermined criteria.

6 Claims, 2 Drawing Sheets

(56) References Cited

U.S. PATENT DOCUMENTS

| | | | | |
|---|---|---|---|---|
| 2013/0125883 | A1* | 5/2013 | Bonassa | A61M 16/024 128/204.23 |
| 2013/0150734 | A1 | 6/2013 | Orr et al. | |
| 2013/0245481 | A1 | 9/2013 | Tremper | |
| 2015/0290407 | A1* | 10/2015 | Bonassa | A61M 16/0833 128/200.24 |
| 2016/0354007 | A1* | 12/2016 | Gärber | A61B 5/742 |
| 2017/0367623 | A1 | 12/2017 | Nakazawa et al. | |
| 2017/0368281 | A1* | 12/2017 | Dermel | A61B 5/08 |
| 2020/0219257 | A1* | 7/2020 | Wang | A61B 5/0816 |
| 2021/0069436 | A1 | 3/2021 | Friberg et al. | |

OTHER PUBLICATIONS

Written Opinion dated Jun. 15, 2022 in International Application No. PCT/BR2022/050058.

* cited by examiner

1

2

1

2

SYSTEM FOR INDICATING AN AT-RISK SITUATION FOR A LUNG VENTILATOR

FIELD OF THE INVENTION

The present invention relates to a system for indicating an at-risk situation for a lung ventilator and, more specifically, to a lung ventilator with a system for indicating an at-risk situation for patient.

BACKGROUND OF THE INVENTION

In general, lung ventilators are equipped with displays that show the ventilation adjustment and monitoring parameters.

The monitored information are usually presented in numerical form or curves in x,y coordinates, which is not always very intuitive or easy to understand.

Several ventilator-derived parameters are shown on ventilators that currently exist by means of a drawing of the lung, airways, blood vessels and the image of the heart, changing the colors or shapes and dimensions of these elements to represent the monitored parameters such as compliance, airway resistance, volume, pressure, among others.

In the event of an emergency event, the delay in understanding what is happening to the lung can delay taking corrective action which, as a consequence, can cause anything from serious lung damage to the patient's death.

Respiratory parameters such as: tidal volume, pressure, compliance, airway resistance and frequency are presented in the form of numbers, graphs or images, which, for each patient there is an ideal value and during ventilation may change depending on the pathology and state of the lung, and ventilation must be readjusted by the physician or physiotherapist, considering, in addition to these factors, the size of the lung that is normally associated with the size of the patient, such as weight and height, which may change depending on lung pathology.

These ideal values are still objects of constant study by the world medical community, however, there is a consensus that the parameters must be adjusted following some criteria of safety limits, for example, for Tidal Volume, relate to the patient's ideal weight. Other protective ventilation criteria may emerge as research advances.

For a person with a certain weight in Kg, with a healthy lung, the Tidal Volume calculated between 6 mL/Kg to 8 mL/Kg is currently considered a safe range. For a diminished lung, for example a patient with ARDS (Acute Respiratory Distress Syndrome) or with a lung with liquids or with atelectasis (collapsed alveoli) or a newborn, it is common to use up to a minimum limit of 4 mL/kg. On the other hand, the higher coefficient is sometimes used when there is C02 retention, which can reach 10 ml_/Kg.

In the currently existing ventilators, the physician or physiotherapist, in order to perceive the risk of barotrauma or hypoventilation, it is necessary to know how to interpret the information on the screen, which is usually shown in the form of curves and numerical parameters that represent the expansion of the lung and parameter values adjusted numerically or in the form of x,y graphs, where normally the x-axis indicates time and the y-axis indicates measured parameter values. There are other forms of graphical representation, such as loops, where the x-axis is another ventilation parameter, making the interpretation even more complex. To understand these graphs, health professionals must have good training and prior knowledge of graph interpretation. In an emergency, the difficult-to-interpret chart can disturb the intensivist and cause harm to the patient. Ventilator in general have alarms, but the operator is not always able to identify the cause of the alarm, as there are many reasons for triggering alarms; depending on the delay in understanding, for example, barotrauma, can result in serious lung damage.

There are lung ventilators, such as the one in the US20090024008A1 patent that uses lung drawings on the screen that vary the size and shape of the outline to help the physician qualitatively visualize the rigidity or elasticity, the resistance of the airways, the blood pressure by changing the width of the tubes; or show lung compliance and resistance by more rounded shape or with sharp corners to indicate harder or more flexible lungs. These used figures using color changes or changes in geometric shapes of the schematic lung showing lung expansion and emptying, which are indicators of mechanical ventilation parameters.

There are other ventilators that, through the drawing of the lung on the screen, qualitatively show inspiration and expiration and, by changing color, they show the pressure in the lung or balls that enter and exit to show the flow of gases. However, they do not show insufficient filling of the lung or the risk of barotrauma.

The alarm limits are usually adjusted manually before connecting to the patient at the discretion of the operator, which may allow an adjustment, for example, above the critical value and end up causing damage to the patient even not reaching the value that triggers the alarm. A distension above the limit value of protective ventilation, even if it does not cause barotrauma, causes injuries that can bring other harmful consequences.

In general, monitors are designed for people with normal vision in terms of color recognition; but, according to the Federal Council of Medicine, around 5% of the population are colorblind. It can be inferred that 5% of physicians and physiotherapists are also color-blind and may misinterpret color-based messages; it is very common to use green for a normal situation and red for a risky situation; with about 70% of colorblind people mistaking green for red, putting patient safety at risk.

Objectives of the Invention

It is one of the objectives of the present invention to provide a system for indicating an at-risk situation for a lung ventilator capable of visually and intuitively warning the intensivist of an at-risk situation to the patient as quickly as possible within the protective ventilation concept point of view.

Another objective of the invention is to avoid wasting time in interpreting numerical data or monitor curves in order to be able to quickly overcome the cause of the risk of non-protective ventilation.

Yet another object of the invention is to protect the patient against improper adjustment of the ventilator or the alarm limits within the concept of protective ventilation.

Yet another objective is to enable health professionals, even those with color blindness, to carry out protective ventilation.

BRIEF DESCRIPTION OF THE INVENTION

The present invention achieves the above objectives by means of a system for indicating an at-risk indication for lung ventilator comprising a screen that displays at least one fixed-size drawing element representing the lungs being ventilated, in which the shade of the drawing element switches according to predetermined criteria.

In one embodiment of the invention, the shade alternation of the fixed-size drawing element is changed between:

a dark shade when a first predetermined criterion is met;

an intermediate shade of the dark color when a second predetermined criterion is met; It is a light shade when a third predetermined criterion is met.

The drawing element may further comprise a broken outline with elements that flash when a fourth predetermined criterion is met.

In one embodiment of the invention, drawing element of fixed size is a drawing of lungs and each of the predetermined criteria is a criterion associated with protective ventilation.

The system for indicating an -at-risk situation for lung ventilators can also comprise a touch sensitive screen.

BRIEF DESCRIPTION OF THE DRAWINGS

The present invention will be described below in more detail, with reference to the accompanying drawings, in which.

DETAILED DESCRIPTION OF THE INVENTION

Figure 1:
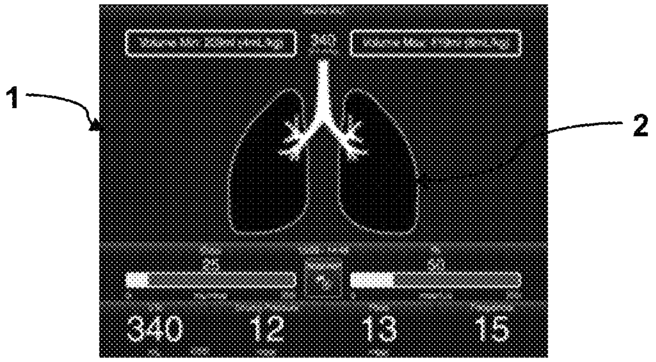
FIG. 1—illustrates the screen of a system for indicating an at-risk situation for a lung ventilator in a first operating condition.

[1] The present invention will be described below based on a embodiment of the invention illustrated in FIGS. 1 to 4.'

FIGS. 1 to 4 show the screen of a lung ventilator. Except for the system for indicating an at-risk situation of the present invention, the ventilator's internal components and their operation are known to those skilled in the art and, therefore, will not be described here.

The system for indicating an at-risk situation of the present invention comprises a screen 1 that displays at least one drawing element of fixed size 2 representing the lungs being ventilated, in which the shade of the drawing element alternates according to predetermined criteria. In the embodiment shown in the figures, the drawing element of fixed size is a drawing of lungs.

Thus, in the illustrated embodiment of the present invention, the shade shift of the fixed size drawing element 2 is changed between:

a dark shade when a predetermined first criterion is met;

an intermediate shade when a second predetermined criterion is met; or a light shade when a third predetermined criterion is met.

In one embodiment of the present invention, the drawing element comprises a broken contour with elements that flash when a fourth predetermined criterion is met.

The predetermined criteria are criteria associated with lung ventilation and, preferably, correspond to insufficient ventilation, ventilation within a safe volume range, and ventilation that exceeds the safe volume limit.

Thus, through the image with shade alternation it is possible to show the expansion and emptying of the lung, showing when properly inflated, when it is above the maximum or below the minimum, whose limits are adjusted based on security criteria that can be configured; as: the predicted volume/weight [mL/Kg] or the calculated driving pressure (driving pressure) or by some other criterion that eventually comes to be accepted and adopted by the medical community as protective.

According to the embodiment illustrated in the figures, three situations that may occur during the operation of the lung ventilator:

If the volume is in the safe range, the shade of the lung (drawing element) changes from black (FIG. 1) to white (FIG. 3) during inspiration, remaining during the inspiratory time, returning to black in the expiration;

When the lung expands beyond the maximum, the contour of the lung will "project rays outwards" (FIG. 4), flashing intermittently to draw the attention of the intensivist to the risk of lung injury due to excessive distension of the alveolus, remaining like this during the inspiratory time, returning to black on expiration;

If the lung volume does not reach the minimum volume required, the black colored lung will show a gray spot (FIG. 2), visually indicating ventilation insufficiency, remaining gray intermittently during the inspiratory time, returning to black on expiration, showing cycling.

The present invention therefore protects in both at-risk situations, barotrauma and insufficient ventilation. In the disconnection condition or another factor that does not inflate the lung, it will remain black, showing that there are no ventilation cycles.

The screen of the illustrated embodiment shows the lungs of a fixed size, colored black during expiration, partially gray when insufficiently inflated and white when properly inflated, and rays coming out of the contour intermittently when excessively full.

In addition, as shown in the figures, the system can also include bar graphs showing compliance and airway resistance, which recalculates and updates whenever the update button is touched.

Figure 2:
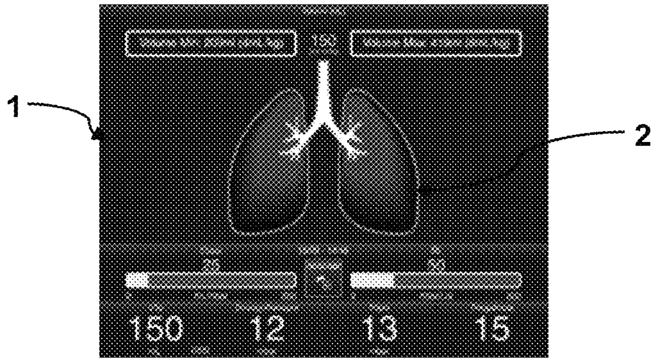
FIG. 2—illustrates the screen of a system for indicating an at-risk situation for a lung ventilator in a second operating condition.
Figure 3:
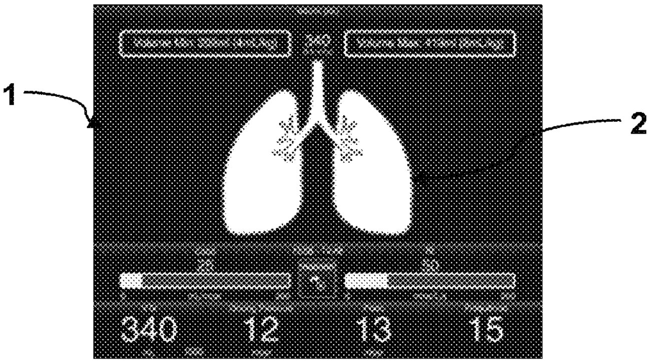
FIG. 3—illustrates the screen of a system for indicating an at-risk situation for a lung ventilator in a third operating condition.
Figure 4:
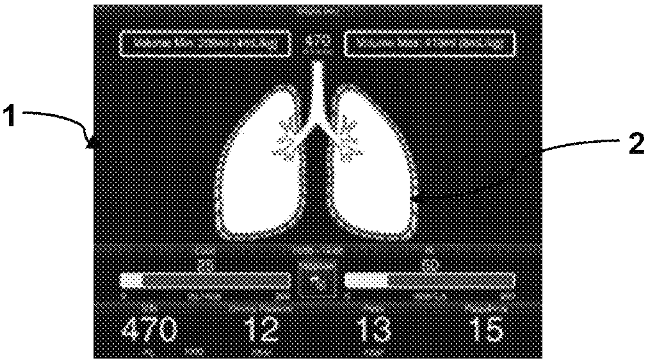
FIG. 4—illustrates the screen of a system for indicating an at-risk situation for a lung ventilator in a fourth operating condition.

As shown in the figures, the lung figures are generated in four types, wherein FIG. 1 shows the lung in black color, FIG. 2 shows the same lung with gray spot, indicating partial filling of the lung, FIG. 3 shows white lung and FIG. 4 shows a white lung with a drawing of white rays, transitioning to dark gray in a tonal gradient, leaving the outline.

FIG. 1 in black is visible during the second half of each monitored exhalation breath cycle, then at the beginning of inspiration FIG. 1 is replaced by FIG. 2 or 3 or 4 depending on the Tidal Volume, if it is below ideal, in the range between the minimum and maximum or above the maximum limit respectively. FIGS. 2 and 3 are visible in the first half of each respiratory cycle. FIG. 4 is visible intermittently during the first half of each cycle.

An important feature of the present invention is that the drawing element comprises a gray color or shade of a single color so that physicians and physiotherapists, even colorblind ones, can understand the ventilation conditions.

Thus, in the illustrated embodiment, the shade of the drawing element in black color or in a dark color indicates empty lung, in gray, or intermediate tone of the dark color used to indicate empty lung, indicates insufficiently inflated lung; and in white color indicates full lung. For the lung inflated above the maximum limit, the design element is shown with the broken outline with "leaking rays".

The broken outline of the drawing element, with "leaking rays", is lit for a fraction of the inspiratory time, flashing, to call the attention of the physician, physiotherapist or nursing staff.

In one embodiment of the invention, the indication system comprises a touch-sensitive monitor screen, with a button designed on the screen to start the static compliance and airway resistance measurement maneuver immediately, updating the values shown in the form of a bar graph, whenever it is activated.

In an embodiment of the invention, the drawing element does not show the respiratory cycles in the absence of expiratory flows.

The criteria for adequate or inadequate ventilation can use protective ventilation as a basis, either in minimum and maximum mL/Kg, or another criterion of protective ventilation, such as "Driving Pressure", or another criterion that come to be defined as protective ventilation.

The present invention allows a quick perception of the risk that the patient's lung is having according to the criteria of protective ventilation, for a quick action to be taken in case, for example, of a risk of barotrauma (rupture of alveoli) or hypoventilation due to insufficient inspired air volume using animated drawing techniques on the image of the lung on the screen.

It should be noted that the present invention represents a way to instantly warn the ventilator operator without the use of colors as risk indicators so that even color-blind health professionals, in a situation of risk to the patient, may make the protective action of the lung more effective.

Having described an example of an exemplary embodiment of the present invention, it should be understood that the scope of the present invention covers other possible variations of the described inventive concept, being limited solely by the content of the attached claims, including the possible equivalents.

The invention claimed is:

1. A system for indicating an at-risk situation for a lung ventilator, said system comprising a screen that displays at least one drawing element of fixed size representing lungs being ventilated, wherein:

shading of the drawing element switches according to predetermined criteria associated with protective ventilation;

a shade alternation of the fixed size drawing element changes between:

a black color shade when a first predetermined criterion is met;

a gray color shade when a second predetermined criterion is met; and a white color shade when a third predetermined criterion is met; and the drawing element further comprises a broken outline with flashing elements when a fourth predetermined criterion is met.

2. The system for indicating an at-risk situation for lung ventilator according to claim 1, wherein the fixed-size drawing element is a drawing of lungs.

3. The system for indicating an at-risk situation for lung ventilator according to claim 1, wherein the screen is a touch screen.

4. A lung ventilator, comprising a system for indicating an at-risk situation with a screen that displays at least one drawing element of fixed size representing lungs being ventilated, wherein:

shading of the drawing element alternates according to predetermined criteria associated with protective ventilation;

a shade alternation of the fixed size drawing element changes between:

a black shade when a first predetermined criterion is met;

a gray shade when a second predetermined criterion is met; and a white shade when a third predetermined criterion is met; and the drawing element further comprises a broken outline with flashing elements when a fourth predetermined criterion is met.

5. The lung ventilator according to claim 4, wherein the fixed-size drawing element is a drawing of lungs.

6. The lung ventilator according to claim 4, wherein the screen is a touch screen.

* * * * *